United States Patent
Kugo

(10) Patent No.: US 11,839,358 B2
(45) Date of Patent: Dec. 12, 2023

(54) RIGIDITY VARIABLE DEVICE AND ENDOSCOPE

(71) Applicant: OLYMPUS CORPORATION, Tokyo (JP)

(72) Inventor: Tomoyuki Kugo, Matsudo (JP)

(73) Assignee: OLYMPUS CORPORATION, Tokyo (JP)

( * ) Notice: Subject to any disclaimer, the term of this patent is extended or adjusted under 35 U.S.C. 154(b) by 555 days.

(21) Appl. No.: 17/109,231

(22) Filed: Dec. 2, 2020

(65) Prior Publication Data
US 2021/0085155 A1    Mar. 25, 2021

Related U.S. Application Data

(63) Continuation of application No. PCT/JP2018/021384, filed on Jun. 4, 2018.

(51) Int. Cl.
| | |
|---|---|
| A61B 1/005 | (2006.01) |
| A61L 29/02 | (2006.01) |
| A61L 29/14 | (2006.01) |
| A61M 25/00 | (2006.01) |

(52) U.S. Cl.
CPC .......... *A61B 1/0055* (2013.01); *A61B 1/0058* (2013.01); *A61L 29/02* (2013.01); *A61L 29/14* (2013.01); *A61L 2400/16* (2013.01); *A61M 25/0054* (2013.01)

(58) Field of Classification Search
CPC ..... A61B 1/0058; A61B 1/0055; A61L 29/02; A61L 29/14; A61L 2400/16; A61M 2025/0064; A61M 25/0054
See application file for complete search history.

(56) References Cited

U.S. PATENT DOCUMENTS

| | | | | |
|---|---|---|---|---|
| 4,427,000 A | * | 1/1984 | Ueda | A61B 17/320016 600/107 |
| 4,924,852 A | * | 5/1990 | Suzuki | A61B 1/0052 600/150 |

(Continued)

FOREIGN PATENT DOCUMENTS

| | | |
|---|---|---|
| JP | H8-110480 A | 4/1996 |
| JP | H11-295615 A | 10/1999 |

(Continued)

OTHER PUBLICATIONS

International Search Report dated Aug. 21, 2018 issued in PCT/JP2018/021384.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

A rigidity variable device includes: a main body unit having an elongated shape; a plurality of higher rigidity portions made of metal, the higher rigidity portions being included in the main body unit and arrayed in a separated manner in a direction along a longitudinal axis of the main body unit; and one or a plurality of lower rigidity portions included in the main body unit and including a shape memory alloy coil disposed between adjacent ones of the higher rigidity portions and formed by winding a wire around an axis parallel to the longitudinal axis. A rigidity of the shape memory alloy coil increases when heated.

4 Claims, 2 Drawing Sheets

(56) References Cited

U.S. PATENT DOCUMENTS

| | | | | | |
|---|---|---|---|---|---|
| 4,930,494 | A | * | 6/1990 | Takehana | A61B 1/0058 600/145 |
| 5,624,380 | A | * | 4/1997 | Takayama | A61B 1/0058 600/141 |
| 5,810,717 | A | * | 9/1998 | Maeda | A61B 1/00193 600/151 |
| 5,996,346 | A | * | 12/1999 | Maynard | B25J 9/06 60/527 |
| 6,485,411 | B1 | * | 11/2002 | Konstorum | A61B 1/00078 604/527 |
| 6,672,338 | B1 | * | 1/2004 | Esashi | A61M 25/0138 138/119 |
| 2002/0142119 | A1 | * | 10/2002 | Seward | A61L 29/126 428/371 |
| 2005/0137456 | A1 | * | 6/2005 | Saadat | A61B 1/00078 600/114 |
| 2005/0182298 | A1 | * | 8/2005 | Ikeda | A61B 34/70 600/104 |
| 2008/0027285 | A1 | * | 1/2008 | Yasunaga | A61B 1/0058 600/150 |
| 2015/0320295 | A1 | * | 11/2015 | Belson | H10N 30/857 600/141 |
| 2018/0080437 | A1 | * | 3/2018 | Morishima | A61B 1/0057 |
| 2019/0255295 | A1 | * | 8/2019 | Spindler | A61M 25/09 |

FOREIGN PATENT DOCUMENTS

| | | |
|---|---|---|
| JP | 2006-334201 A | 12/2006 |
| JP | 2008-23089 A | 2/2008 |
| WO | 2016/174741 A1 | 11/2016 |

* cited by examiner

US 11,839,358 B2

RIGIDITY VARIABLE DEVICE AND ENDOSCOPE

CROSS REFERENCE TO RELATED APPLICATION

This application is a continuation application of PCT/JP2018/021384 filed on Jun. 4, 2018, the entire contents of which are incorporated herein by this reference.

BACKGROUND OF THE INVENTION

1. Field of the Invention

The present invention relates to a rigidity variable device and an endoscope using a shape memory alloy.

2. Description of the Related Art

As disclosed in International Publication No. WO 2016/174741, for example, a rigidity variable device using a shape memory alloy has been proposed in which an elongated shape memory member and a heating coil independent from the shape memory member are provided and the shape memory member is heated by the heating coil to increase the rigidity.

SUMMARY OF THE INVENTION

A rigidity variable device according to an aspect of the present invention includes: a main body unit having an elongated shape; a plurality of higher rigidity portions made of metal, the higher rigidity portions being included in the main body unit and arrayed in a separated manner in a direction along a longitudinal axis of the main body unit; and one or a plurality of lower rigidity portions included in the main body unit and including a shape memory alloy coil disposed between adjacent ones of the higher rigidity portions and formed by winding a wire around an axis parallel to the longitudinal axis. A rigidity of the shape memory alloy coil increases when heated.

An endoscope according to an aspect of the present invention includes: an insertion portion inserted into a subject; and the rigidity variable device.

DETAILED DESCRIPTION OF THE PREFERRED EMBODIMENT

Figure 1:
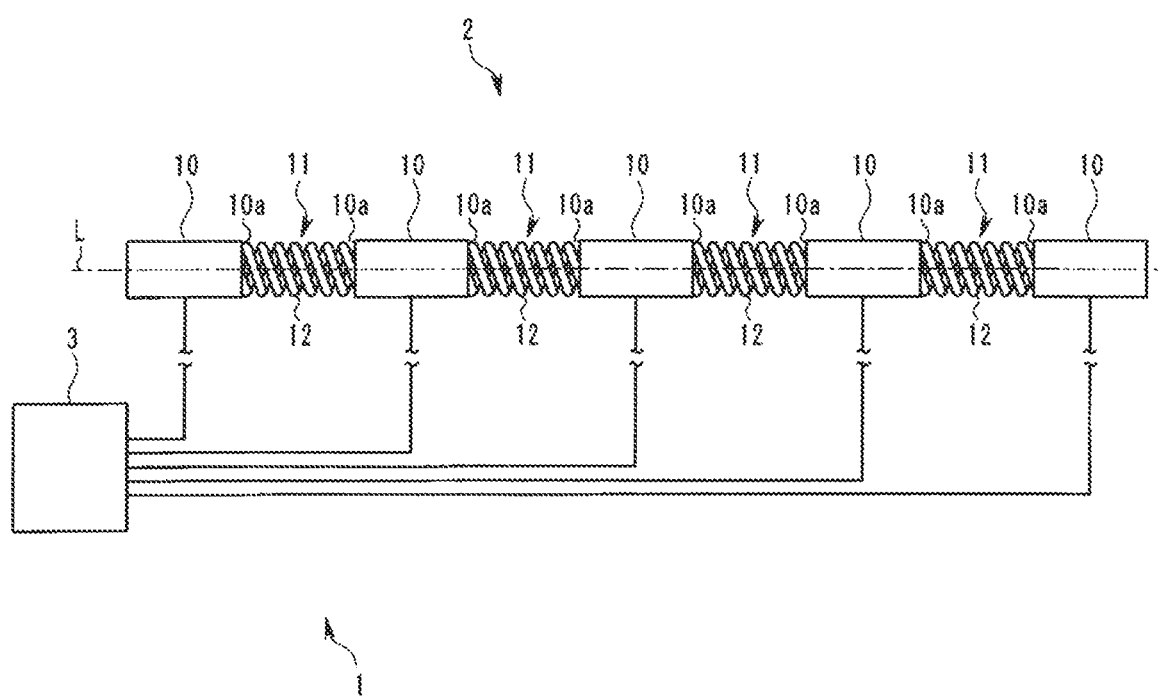
FIG. 1 is a diagram illustrating a configuration of a rigidity variable device.

A preferred embodiment of the present invention will be described below with reference to the drawings. Note that the scale of each component in each figure used in the following description is altered in order for the component to have a recognizable size in the figure, and the present invention is not limited to the number of components, the shapes of the components, the ratio of the sizes of the components, and the relative positional relationships between the individual components indicated in the figures.

An example embodiment of the present invention will be described below. A rigidity variable device 1 shown in FIG. 1 includes a main body unit 2 and an energizing member 3.

The main body unit 2 has an elongated shape along a longitudinal axis L. The rigidity variable device 1 can change rigidity in response to an input of force in a direction to bend the longitudinal axis L of the main body unit 2. The rigidity refers to resistance to bending deformation of the main body unit 2 having the elongated shape. The rigidity is represented by force needed to bend a section having a predetermined length in a direction along the longitudinal axis L of the main body unit 2 by a predetermined curvature. Thus, the higher the rigidity is, the harder the main body unit 2 deforms in the bending direction.

The main body unit 2 includes a plurality of higher rigidity portions 10 and a plurality of lower rigidity portions 11. The plurality of higher rigidity portions 10 are arrayed in line along the longitudinal axis L. Portions of a pair of adjacent higher rigidity portions 10 facing each other are referred to as end portions 10a.

A gap is provided between the facing end portions 10a of the pair of adjacent higher rigidity portions 10. A lower rigidity portion 11 is arranged at the gap provided between the pair of adjacent higher rigidity portions 10.

In other words, the end portions 10a of the pair of higher rigidity portions 10 are arranged at both sides of the lower rigidity portion 11 in the direction along the longitudinal axis L. The lower rigidity portions 11 are fixed at both end portions 10a of the pair of adjacent higher rigidity portions 10. Thus, the main body unit 2 is configured by alternately connecting the higher rigidity portions 10 and the lower rigidity portions 11 to each other in the direction along the longitudinal axis L.

Note that the numbers of higher rigidity portions 10 and lower rigidity portions 11 included in the main body unit 2 are not particularly limited. Although five higher rigidity portions 10 and four lower rigidity portions 11 are shown in FIG. 1 as an example in the present embodiment, the numbers of higher rigidity portions 10 and lower rigidity portions 11 may be more or less than in the present embodiment shown in FIG. 1.

Note that the terms "higher rigidity" and "lower rigidity" in referring to the higher rigidity portions 10 and the lower rigidity portions 11 are used to represent a relative difference in rigidity between them, which will be described in detail later. Therefore, these terms do not limit the absolute values of the rigidities of the higher rigidity portions 10 and the lower rigidity portions 11.

The higher rigidity portions 10 are made of metal and have electrical conductivity. Although the shape of the higher rigidity portions 10 is not particularly limited, the higher rigidity portions 10 have a columnar shape. In the present embodiment, as an example, the higher rigidity portions 10 have a cylindrical shape, and are arranged in an orientation to have a circular shape as seen in the direction along the longitudinal axis L. Note that the higher rigidity portions 10 may contain a material other than metal. For example, the higher rigidity portions 10 may be formed by curing an electrically conductive adhesive containing particles made of metal.

The lower rigidity portion 11 includes a shape memory alloy coil (hereinafter referred to as an SMA coil) 12. The SMA coil 12 is formed by helically winding one or more wires made of a shape memory alloy around an axis parallel to the longitudinal axis L. In other words, the SMA coil 12 is not limited to a single helix shape and may have a double helix shape, a triple helix shape, or the like.

The SMA coil 12 is disposed between end portions 10a of a pair of adjacent higher rigidity portions 10. The SMA coil 12 is fixed to both of the pair of higher rigidity portions 10.

The method of fixing the SMA coil 12 and the higher rigidity portions 10 is not particularly limited. In the present embodiment, as an example, the SMA coil 12 and the higher rigidity portions 10 are fixed with an electrically conductive adhesive. Note that the fixing of the SMA coil 12 and the higher rigidity portions 10 may be performed by swaging or soldering, for example.

The shape memory alloy, which is a known technology and is not described in detail, experiences a phase change at a predetermined temperature T and changes in elastic modulus. The SMA coil 12 of the present embodiment experiences a phase change at a predetermined temperature T exceeding a room temperature. The elastic modulus of the SMA coil 12 at a temperature higher than or equal to the predetermined temperature T is higher than the elastic modulus of the SMA coil 12 at a temperature lower than the predetermined temperature T. The SMA coil 12 exhibits super elasticity at a temperature higher than or equal to the predetermined temperature T.

The shape memorized by the SMA coil 12 is a shape formed by winding a wire around a straight-line shaped axis. In other words, at a temperature higher than or equal to the predetermined temperature T and when no external force is applied, the SMA coil 12 has a shape having a center axis on a straight line parallel to the longitudinal axis L of the main body unit 2 as shown in FIG. 1.

The SMA coil 12 is electrically connected to the energizing member 3, which will be described later. By being heated by energization, the SMA coil 12 generates heat to a temperature exceeding the predetermined temperature T at which the phase change occurs.

The plurality of lower rigidity portions 11 included in the main body unit 2 may have respective different SMA coils 12, or may share the same SMA coil 12. For example, in the present embodiment, each of the plurality of lower rigidity portions 11 may have a unique SMA coil 12 independently from each other.

For example, at least two lower rigidity portions 11 of the plurality of lower rigidity portions 11 may be configured by a common SMA coil 12. In this case, the SMA coil 12 penetrates the higher rigidity portion 10 interposed between the two lower rigidity portions 11.

The energizing member 3 switches between energization and non-energization of the SMA coil 12. Note that the energizing member 3 may or may not include a power supply as long as the energizing member 3 has a switching function for switching between energization and non-energization based on an instruction from a user or other electronic equipment. When energized by an operation of the energizing member 3, the SMA coil 12 is heated by the energization to reach a temperature higher than or equal to the predetermined temperature T.

Note that the energizing member 3 may only have a configuration to collectively switch the energization of SMA coils 12 included in all lower rigidity portions 11 of the plurality of lower rigidity portions 11, or may further have a configuration to switch the energization of SMA coils 12 included in some selected lower rigidity portions 11 of the plurality of lower rigidity portions 11.

In the present embodiment illustrated in the figure, as an example, the energizing member 3 is electrically connected to the plurality of higher rigidity portions 10, and is electrically connected to a plurality of SMA coils 12 via the plurality of higher rigidity portions 10. The energizing member 3 can select an SMA coil 12 to be energized from the plurality of SMA coils 12.

In the rigidity variable device 1 having the above-described configuration, when the SMA coil 12 is not energized, the temperature of the SMA coil 12 is lower than the predetermined temperature T, and the elastic modulus of the SMA coil 12 takes a low state. In the rigidity variable device 1, when the SMA coil 12 is energized, the temperature of the SMA coil 12 is higher than or equal to the predetermined temperature T, and the elastic modulus of the SMA coil 12 takes a high state.

Therefore, in the rigidity variable device 1 of the present embodiment, among the higher rigidity portions 10 and the lower rigidity portions 11 alternately connected along the longitudinal axis L, the lower rigidity portions 11 changes in rigidity.

Since the higher rigidity portions 10 are columnar members made of metal, the higher rigidity portions 10 substantially behave as rigid bodies even when force in the direction to bend the longitudinal axis L of the main body unit 2 is inputted.

Since the lower rigidity portions 11 are configured by the SMA coil 12, even if the elastic modulus of the SMA coil 12 is in the high state, the lower rigidity portions 11 elastically deforms in the bending direction when force in the direction to bend the longitudinal axis L of the main body unit 2 is inputted. Therefore, in the rigidity variable device 1 of the present embodiment, the rigidity of the main body unit 2 changes in response to the switching between energization and non-energization of the plurality of SMA coils 12.

Since the main body unit 2 has a configuration in which the plurality of higher rigidity portions 10 are connected by the plurality of SMA coils 12, the rigidity of the entire main body unit 2 is higher than the rigidity of an SMA coil having the same length as the main body unit 2.

Here, the SMA coil 12 configuring the lower rigidity portions 11 of the present embodiment has a shape in which a wire is wound around an axis parallel to the longitudinal axis L. Thus, when the main body unit 2 deforms in the bending direction, the wire of the SMA coil 12 elastically deforms in a torsional direction. Therefore, the SMA coil 12 has a larger angle by which the SMA coil 12 can elastically deform in the bending direction than in the case where a straight-line shaped SMA wire is disposed between the pair of higher rigidity portions 10. Thus, the SMA coil 12 is less prone to plastic deformation even when the main body unit 2 deforms in the bending direction by a large curvature. In other words, the SMA coil 12 is less prone to create a bending trace.

Since the SMA coil 12 has a small diameter, the lower rigidity portions 11 of the present embodiment have a smaller bending stress in the SMA coil 12 at a predetermined angle and hence a larger angle by which the lower rigidity portions 11 can elastically deform in the bending direction than in the case where a straight-line shaped shape memory alloy member having a larger diameter is disposed between the pair of higher rigidity portions 10, for example. In other words, the small diameter of the SMA coil 12 also allows the lower rigidity portions 11 to exhibit an effect of resistance to permanent set or rupture even when the main body unit 2 deforms in the bending direction by a large curvature.

The length of the wire configuring the SMA coil 12 is larger than in the case where a straight-line shaped shape memory alloy member is disposed between the pair of higher rigidity portions 10 in a direction parallel to the longitudinal axis L. Thus, the SMA coil 12 has a high electrical resistance and easily increases in temperature by being heated by energization.

In the present embodiment, the SMA coil 12 configuring the lower rigidity portions 11 is formed of a linear member and hence has a small thermal capacity. Therefore, it takes little time to cool the SMA coil 12 from a temperature higher than or equal to the predetermined temperature T to a temperature lower than the predetermined temperature. Thus, in the rigidity variable device 1 of the present embodiment, the switching from the state where the rigidity of the main body unit 2 is increased to the state where the rigidity of the main body unit 2 is decreased can be performed quickly.

As described above, the rigidity variable device 1 of the present embodiment can achieve both of obtaining a high rigidity when the rigidity of the main body unit 2 is increased and quickly decreasing the rigidity.

Since the rigidity variable device 1 of the present embodiment is configured by the SMA coil 12 having a small diameter, a less electric power is needed for heating than in the case where a straight-line shaped shape memory alloy member having a larger diameter is disposed between the pair of higher rigidity portions 10, for example. Therefore, it is easy to heat the SMA coil 12 by the energization of the SMA coil 12 to a temperature higher than or equal to the predetermined temperature T, and thus the need for a heater for heating the SMA coil 12 can be eliminated.

Figure 2:
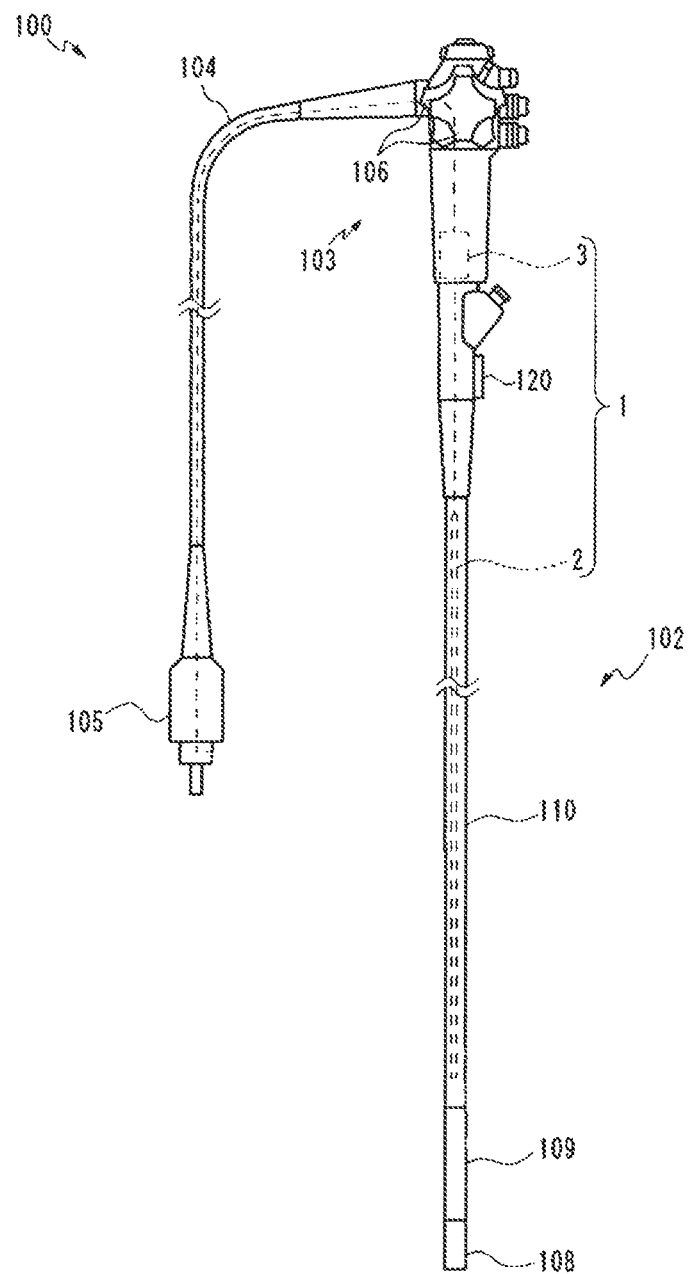
FIG. 2 is a diagram illustrating a configuration of an endoscope.

FIG. 2 illustrates an endoscope 100 including the rigidity variable device 1. The endoscope 100 includes an insertion portion 102 having an elongated shape and having flexibility that can be inserted into a subject such as a human body, and includes a component for observing the inside of the subject in the insertion portion 102. Note that the subject into which the insertion portion 102 of the endoscope 100 is inserted is not limited to a human body, and may be another organism or may be an artifact such as a machine or a building.

The endoscope 100 of the present embodiment is mainly configured by the insertion portion 102, an operation portion 103 positioned at a proximal end of the insertion portion 102, and a universal cord 104 extending from the operation portion 103.

The insertion portion 102 is configured by connecting a distal end portion 108 provided at a distal end, a bending portion 109 that is bendable and is provided at a proximal end side of the distal end portion 108, and a flexible tube portion 110 having flexibility and connecting a proximal end side of the bending portion 109 and a distal end side of the operation portion 103.

A component for observing the inside of the subject or the like is provided at the distal end portion 108. For example, an image pickup unit for optically observing the inside of the subject, which includes an object lens and an image pickup device, is provided at the distal end portion 108. An illumination light emitting unit for emitting light, which is not shown, for illuminating an object of the image pickup unit is also provided at the distal end portion 108. Note that an ultrasound transducer for acoustically observing the inside of the subject by means of ultrasound may also be provided at the distal end portion 108.

The main body unit 2 of the rigidity variable device 1 is inserted into at least one of the bending portion 109 and the flexible tube portion 110, which are portions of the insertion portion 102 that are capable of bending deformation. In the present embodiment illustrated in the figure, as an example, the main body unit 2 is arranged in the flexible tube portion 110.

An angle control knob 106 for controlling the bending of the bending portion 109 is provided in the operation portion 103 provided at the proximal end portion of the insertion portion 102. An endoscope connector 105 configured to be connectable with an external device, which is not shown, is provided at a proximal end portion of the universal cord 104. The external device to which the endoscope connector 105 is connected includes a camera control unit for controlling the image pickup unit provided in the distal end portion 108, and the like.

The energizing member 3 of the rigidity variable device 1 and a rigidity changing switch 120 for controlling the energizing member 3 are provided in the operation portion 103. The rigidity changing switch 120 controls the operation of the energizing member 3 for switching between energization and non-energization of the SMA coil 12.

The energizing member 3 is arranged in the operation portion 103. The energizing member 3 is electrically connected to an electrical contact provided to the endoscope connector 105 via an electrical cable inserted into the universal cord 104. The electric power for heating the SMA coil 12 of the rigidity variable device 1 by energization is supplied from the external device to which the endoscope connector 105 is connected. Note that the endoscope 100 may also include a battery for supplying electric power for heating the SMA coil 12 of the rigidity variable device 1 by energization.

The endoscope 100 having the above-described configuration can change the rigidity of the insertion portion 102 having flexibility and an elongated shape in response to an operation of the rigidity changing switch 120 by the user.

As described above, the rigidity variable device 1 of the present embodiment can achieve both of obtaining a high rigidity when the rigidity of the main body unit 2 is increased and quickly decreasing the rigidity. Therefore, the endoscope 100 can achieve both of increasing the variable range of the rigidity of the insertion portion 102 and shortening the time period needed for changing the rigidity.

The present invention is not limited to the above-described embodiment and can be changed as appropriate without departing from the gist and idea of the invention that can be read from the claims and the entire specification, and a rigidity variable device and an endoscope with such changes are also included in the technical scope of the present invention.

What is claimed is:

1. A rigidity variable device comprising:
   a main body having an elongated shape;
   a plurality of higher rigidity portions made of metal, the plurality of higher rigidity portions being included in the main body and arrayed in a separated manner in a direction along a longitudinal axis of the main body;
   one or more lower rigidity portions included in the main body, the one or more lower rigidity portions comprising a shape memory alloy coil disposed between adjacent ones of the plurality of higher rigidity portions and the shape memory coil including a wire wound around an axis parallel to the longitudinal axis, a rigidity of the shape memory alloy coil increasing when heated; and
   a switch configured to switch between energization and non-energization of the shape memory alloy coil;
   wherein the switch is electrically connected to the plurality of higher rigidity portions and is electrically connected to the shape memory alloy coil via the plurality of higher rigidity portions; and
   the shape memory alloy coil is heated by the energization.

2. The rigidity variable device according to claim 1, wherein the plurality of higher rigidity portions comprising three or more higher rigidity portions and the one or more lower rigidity portions comprising two or more lower rigidity portions.

3. The rigidity variable device according to claim 2, wherein the two or more lower rigidity portions share the same shape memory alloy coil.

4. An endoscope comprising:
an insertion portion inserted into a subject; and
the rigidity variable device according to claim 1 disposed in the insertion portion.

* * * * *